United States Patent
Dickens et al.

(10) Patent No.: US 8,187,266 B2
(45) Date of Patent: May 29, 2012

(54) SURGICAL PROBE AND METHODS FOR TARGETED TREATMENT OF HEART STRUCTURES

(75) Inventors: Duane Dickens, San Clemente, CA (US); Thomas Witzel, Laguna Niguel, CA (US)

(73) Assignee: QuantumCor, Inc., San Clemente, CA (US)

( * ) Notice: Subject to any disclaimer, the term of this patent is extended or adjusted under 35 U.S.C. 154(b) by 1522 days.

(21) Appl. No.: 11/537,561

(22) Filed: Sep. 29, 2006

(65) Prior Publication Data

US 2008/0082099 A1 Apr. 3, 2008

(51) Int. Cl.
   *A61B 18/18* (2006.01)
   *A61F 2/00* (2006.01)
(52) U.S. Cl. .............. 606/41; 606/45; 606/49; 607/101; 607/102
(58) Field of Classification Search .......... 606/110–113, 606/45–50, 41, 42; 607/101–102
See application file for complete search history.

(56) References Cited

U.S. PATENT DOCUMENTS

| | | |
|---|---|---|
| 4,215,015 A | 7/1980 | Tu |
| 4,238,243 A | 12/1980 | Tu et al. |
| 4,239,615 A | 12/1980 | Tu |
| 4,250,059 A | 2/1981 | Tu |
| 4,261,861 A | 4/1981 | Tu et al. |
| 4,263,174 A | 4/1981 | Tu et al. |
| 4,264,473 A | 4/1981 | Tu et al. |
| 4,280,897 A | 7/1981 | Shah et al. |
| 4,291,186 A | 9/1981 | Tu |
| 4,295,955 A | 10/1981 | Tu |
| 4,299,688 A | 11/1981 | Tu et al. |
| 4,299,733 A | 11/1981 | Tu |
| 4,300,012 A | 11/1981 | Tu et al. |
| 4,305,845 A | 12/1981 | Tu |
| 4,312,743 A | 1/1982 | Tu et al. |
| 4,312,744 A | 1/1982 | Tu et al. |
| 4,316,819 A | 2/1982 | Tu et al. |
| 4,333,821 A | 6/1982 | Tu |
| 4,337,145 A | 6/1982 | Tu |
| 4,343,723 A | 8/1982 | Rogers et al. |
| 4,345,946 A | 8/1982 | Tu et al. |
| 4,348,272 A | 9/1982 | Tu |
| 4,364,847 A | 12/1982 | Tu |
| 4,493,320 A * | 1/1985 | Treat ................ 606/47 |
| 4,816,339 A | 3/1989 | Tu et al. |
| 4,882,113 A | 11/1989 | Tu et al. |
| 4,905,691 A * | 3/1990 | Rydell ............. 606/47 |
| 5,024,671 A | 6/1991 | Tu et al. |
| 5,061,276 A | 10/1991 | Tu et al. |
| 5,071,609 A | 12/1991 | Tu et al. |
| 5,318,564 A * | 6/1994 | Eggers ............. 606/47 |
| 5,376,110 A | 12/1994 | Tu et al. |
| 5,549,666 A | 8/1996 | Hata et al. |

(Continued)

*Primary Examiner* — Roy Gibson
(74) *Attorney, Agent, or Firm* — Cotman IP Law Group, PLC

(57) ABSTRACT

A surgical probe and methods for targeted treatment of structures of the heart with heat and radiofrequency energy. The probe which is designed to operated by hand has a elongate member with a handle and an energy-delivering member in an adjustable loop configuration. The control placed on the handle allow the user to alter the length of the loop configuration of the energy-delivering member and to thus place energy-delivering elements located on the energy-delivering member at selected or targeted portions of the heart or structures within the heart. The elongate member is conformable and can be bent into different configurations to allow additional targeted treatment of the particular portions of the heart.

11 Claims, 2 Drawing Sheets

U.S. PATENT DOCUMENTS

| | | | |
|---|---|---|---|
| 5,769,780 A | 6/1998 | Hata et al. | |
| 5,779,715 A | 7/1998 | Tu | |
| 5,782,900 A | 7/1998 | de la Rama et al. | |
| 5,792,140 A | 8/1998 | Tu et al. | |
| 5,843,020 A | 12/1998 | Tu et al. | |
| 5,843,152 A | 12/1998 | Tu et al. | |
| 5,868,741 A | 2/1999 | Chia et al. | |
| 5,876,340 A | 3/1999 | Tu et al. | |
| 5,876,399 A | 3/1999 | Chia et al. | |
| 5,891,027 A | 4/1999 | Tu et al. | |
| 5,891,137 A | 4/1999 | Chia et al. | |
| 5,891,138 A | 4/1999 | Tu et al. | |
| 5,893,884 A | 4/1999 | Tu | |
| 5,897,554 A | 4/1999 | Chia et al. | |
| 5,913,856 A | 6/1999 | Chia et al. | |
| 5,938,658 A | 8/1999 | Tu | |
| 5,938,659 A | 8/1999 | Tu et al. | |
| 5,941,845 A | 8/1999 | Tu et al. | |
| 5,948,009 A | 9/1999 | Tu | |
| 5,951,471 A | 9/1999 | de la Rama et al. | |
| 5,954,649 A | 9/1999 | Chia et al. | |
| 5,957,862 A | 9/1999 | Lu et al. | |
| 5,968,005 A | 10/1999 | Tu | |
| 5,971,968 A | 10/1999 | Tu et al. | |
| 5,980,515 A | 11/1999 | Tu et al. | |
| 5,980,563 A | 11/1999 | Tu et al. | |
| 5,989,248 A | 11/1999 | Tu et al. | |
| 5,992,418 A | 11/1999 | de la Rama et al. | |
| 5,997,534 A | 12/1999 | Tu et al. | |
| 6,001,095 A | 12/1999 | de la Rama et al. | |
| 6,006,123 A | 12/1999 | Nguyen et al. | |
| 6,016,437 A | 1/2000 | Tu et al. | |
| 6,017,324 A | 1/2000 | Tu et al. | |
| 6,024,742 A | 2/2000 | Tu et al. | |
| 6,033,402 A | 3/2000 | Tu et al. | |
| 6,033,403 A | 3/2000 | Tu et al. | |
| 6,036,689 A | 3/2000 | Tu et al. | |
| 6,050,993 A | 4/2000 | Tu et al. | |
| 6,053,913 A | 4/2000 | Tu et al. | |
| 6,068,645 A | 5/2000 | Tu | |
| 6,071,279 A * | 6/2000 | Whayne et al. | 606/41 |
| 6,077,298 A | 6/2000 | Tu et al. | |
| 6,090,134 A | 7/2000 | Tu et al. | |
| 6,096,033 A | 8/2000 | Tu et al. | |
| 6,102,908 A | 8/2000 | Tu et al. | |
| 6,104,952 A | 8/2000 | Tu et al. | |
| 6,113,593 A | 9/2000 | Tu et al. | |
| 6,123,703 A | 9/2000 | Tu et al. | |
| 6,123,718 A | 9/2000 | Tu et al. | |
| 6,129,725 A | 10/2000 | Tu et al. | |
| 6,149,647 A | 11/2000 | Tu et al. | |
| 6,156,033 A | 12/2000 | Tu et al. | |
| 6,161,548 A | 12/2000 | Tu | |
| 6,165,206 A | 12/2000 | Tu | |
| 6,179,789 B1 | 1/2001 | Tu et al. | |
| 6,206,842 B1 | 3/2001 | Tu et al. | |
| 6,217,576 B1 | 4/2001 | Tu et al. | |
| 6,221,070 B1 | 4/2001 | Tu et al. | |
| 6,226,554 B1 | 5/2001 | Tu et al. | |
| 6,228,109 B1 | 5/2001 | Tu et al. | |
| 6,231,570 B1 | 5/2001 | Tu et al. | |
| 6,233,477 B1 | 5/2001 | Chia et al. | |
| 6,235,024 B1 | 5/2001 | Tu et al. | |
| 6,238,390 B1 | 5/2001 | Tu et al. | |
| 6,241,692 B1 | 6/2001 | Tu et al. | |
| 6,241,726 B1 | 6/2001 | Chia et al. | |
| 6,241,727 B1 | 6/2001 | Tu et al. | |
| 6,245,067 B1 | 6/2001 | Tu et al. | |
| 6,246,899 B1 | 6/2001 | Chia et al. | |
| 6,246,914 B1 | 6/2001 | de la Rama et al. | |
| 6,259,941 B1 | 7/2001 | Chia et al. | |
| 6,267,781 B1 | 7/2001 | Tu | |
| 6,283,962 B1 | 9/2001 | Tu et al. | |
| 6,290,697 B1 | 9/2001 | Tu et al. | |
| 6,306,133 B1 | 10/2001 | Tu et al. | |
| 6,308,090 B1 | 10/2001 | Tu et al. | |
| 6,319,251 B1 | 11/2001 | Tu et al. | |
| 6,322,583 B1 | 11/2001 | Tu et al. | |
| 6,346,105 B1 | 2/2002 | Tu et al. | |
| 6,406,493 B1 | 6/2002 | Tu et al. | |
| 6,423,023 B1 | 7/2002 | Chang et al. | |
| 6,451,011 B2 | 9/2002 | Tu | |
| 6,485,489 B2 | 11/2002 | Teirstein et al. | |
| 6,506,398 B1 | 1/2003 | Tu et al. | |
| 6,551,312 B2 | 4/2003 | Zhang et al. | |
| 6,569,163 B2 | 5/2003 | Hata et al. | |
| 6,575,971 B2 | 6/2003 | Hauck et al. | |
| 6,624,138 B1 | 9/2003 | Sung et al. | |
| 6,666,841 B2 | 12/2003 | Gharib et al. | |
| 6,682,558 B2 | 1/2004 | Tu et al. | |
| 6,685,702 B2 | 2/2004 | Quijano et al. | |
| 6,736,791 B1 | 5/2004 | Tu et al. | |
| 6,805,711 B2 | 10/2004 | Quijano et al. | |
| 6,807,444 B2 | 10/2004 | Tu et al. | |
| 6,830,585 B1 | 12/2004 | Artof et al. | |
| 6,830,586 B2 | 12/2004 | Quijano et al. | |
| 6,832,111 B2 | 12/2004 | Tu et al. | |
| 6,875,231 B2 | 4/2005 | Anduiza et al. | |
| 6,926,715 B1 | 8/2005 | Hauck et al. | |
| 6,939,359 B2 | 9/2005 | Tu et al. | |
| 6,949,518 B1 | 9/2005 | Chu et al. | |
| 6,960,178 B2 | 11/2005 | Chang et al. | |
| 6,964,661 B2 * | 11/2005 | Rioux et al. | 606/41 |
| 6,969,367 B2 | 11/2005 | Tu et al. | |
| 6,974,464 B2 | 12/2005 | Quijano et al. | |
| 6,981,958 B1 | 1/2006 | Gharib et al. | |
| 6,998,418 B1 | 2/2006 | Sung et al. | |
| 7,004,911 B1 | 2/2006 | Tu et al. | |
| 7,029,675 B1 | 4/2006 | Lin et al. | |
| 7,041,132 B2 | 5/2006 | Quijano et al. | |
| 7,052,495 B2 * | 5/2006 | Smith | 606/47 |
| 7,060,684 B1 | 6/2006 | Quijano et al. | |
| 7,094,225 B2 | 8/2006 | Tu et al. | |
| 7,101,857 B2 | 9/2006 | Sung et al. | |
| 7,135,009 B2 | 11/2006 | Tu et al. | |
| 7,153,299 B1 | 12/2006 | Tu et al. | |
| 7,163,543 B2 | 1/2007 | Smedley et al. | |
| 7,175,619 B2 * | 2/2007 | Koblish et al. | 606/41 |
| 7,186,232 B1 | 3/2007 | Smedley et al. | |
| 7,229,469 B1 | 6/2007 | Witzel et al. | |
| 2003/0060822 A1 * | 3/2003 | Schaer et al. | 606/41 |
| 2005/0240249 A1 | 10/2005 | Tu et al. | |

* cited by examiner

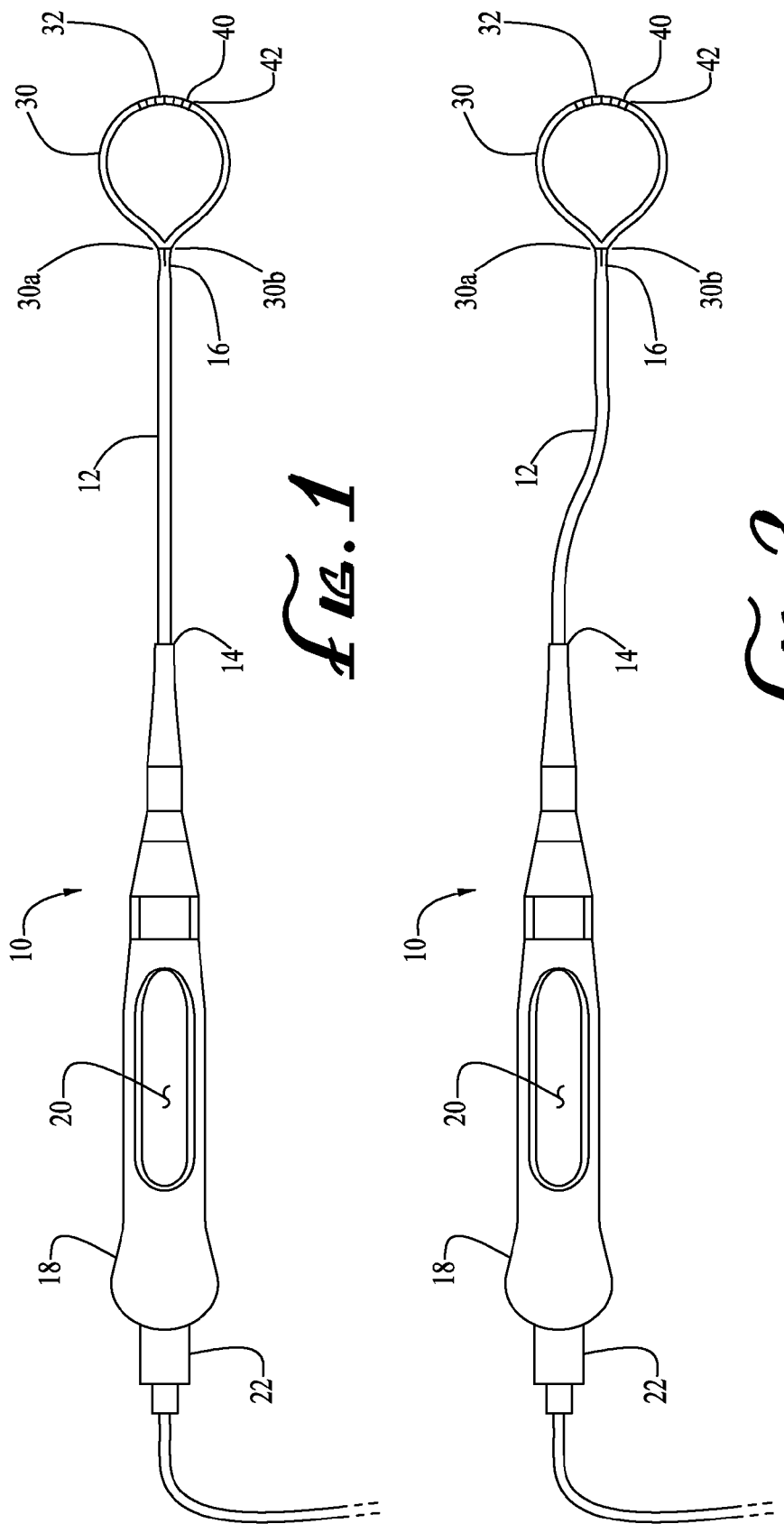

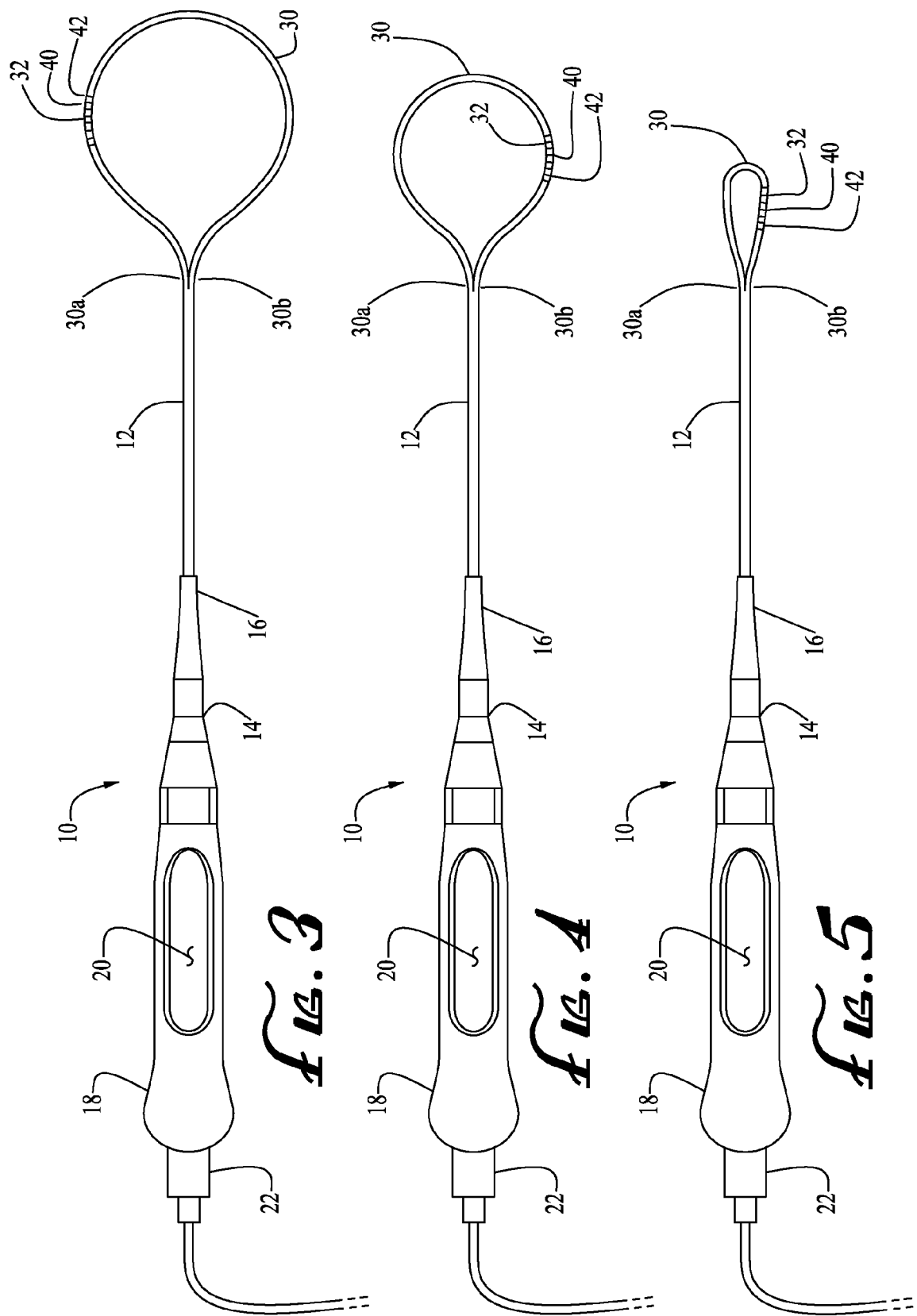

SURGICAL PROBE AND METHODS FOR TARGETED TREATMENT OF HEART STRUCTURES

BACKGROUND OF THE INVENTION

1. Field of the Invention

The present invention generally relates to a surgical probe for treating and repairing heart structures and more particularly, relates to a surgical probe for treating and repairing tissues and anatomic structures within the heart with heat and radiofrequency energy.

2. Description of the Related Art

It is estimated over twelve million people around the world suffer from Congestive Heart Failure (CHF). CHF is a family of related conditions defined by the failure of the heart to pump blood efficiently resulting in congestion (or backing up of the blood) in the lungs or peripheral circulation. CHF can ultimately lead to end-organ failure, which contributes to death of the patient. The heart muscle of the CHF patient may be altered with the chambers dilated and the heart walls thickened or thinned. CHF can result from several conditions, including infections of the heart muscle or valve, physical damage to the valve or by damaged muscle caused by infarction (heart attack).

CHF is the fastest growing cardiovascular disease with over 1 million new cases occurring each year. Conservative estimates suggest that the prevalence of CHF will more than double by 2007. If untreated, CHF may result in severe lifestyle restrictions and ultimately death. One of the causes of CHF and a very common contributor to the harmful effects of CHF is a leaky mitral heart valve. The mitral valve is located in the center of the heart between the two left or major heart chambers and plays an important role in maintaining forward flow of blood. The medical term for this leaky condition is "mitral regurgitation" and the condition affects well over one million people globally. Mitral regurgitation is also called 'mitral incompetence' or 'mitral insufficiency'.

For general background information, the circulatory system consists of a heart and blood vessels. In its path through the heart, the blood encounters four valves. The valve on the right side that separates the right atrium from the right ventricle has three cusps and is called the tricuspid valve. It closes when the ventricle contracts during a phase known as systole and it opens when the ventricle relaxes, a phase known as diastole.

The pulmonary valve separates the right ventricle from the pulmonary artery. It opens during systole, to allow the blood to be pumped toward the lungs, and it closes during diastole to keep the blood from leaking back into the heart from the pulmonary artery. The pulmonary valve has three cusps, each one resembling a crescent and it is also known as a semi-lunar valve.

The two-cusped mitral valve, so named because of its resemblance to a bishop's mitre, is in the left ventricle and it separates the left atrium from the ventricle. It opens during diastole to allow the blood stored in the atrium to pour into the ventricle, and it closes during systole to prevent blood from leaking back into the atrium. The mitral valve and the tricuspid valve differ significantly in anatomy. The annulus of the mitral valve is somewhat D-shaped whereas the annulus of the tricuspid valve is more nearly circular.

The fourth valve is the aortic valve. It separates the left ventricle from the aorta. It has three semi-lunar cusps and it closely resembles the pulmonary valve. The aortic valve opens during systole allowing a stream of blood to enter the aorta and it closes during diastole to prevent any of the blood from leaking back into the left ventricle. In a venous circulatory system, a venous valve functions to prevent the venous blood from leaking back into the upstream side so that the venous blood can return to the heart and the lungs for blood oxygenating purposes.

Clinical experience has shown that repair of a valve, either a heart valve or a venous valve, produces better long-term results than does valve replacement. Valve replacement using a tissue valve suffers long-term calcification problems. On the other hand, anticoagulation medicine, such as cumadin, is required for the life of a patient when a mechanical valve is used in valve replacement. The current technology for valve repair or valve replacement requires an expensive open-heart surgery that needs a prolonged period of recovery. A less invasive repair technology presents an unmet clinical challenge.

The effects of valvular dysfunction vary. Mitral regurgitation may have more severe physiological consequences to the patient than does tricuspid valve regurgitation. In patients with valvular insufficiency, it is an increasingly common surgical practice to repair the natural valve, and to attempt to correct the defects. Many of the defects are associated with dilation of the valve annulus. This dilatation not only prevents competence of the valve but also results in distortion of the normal shape of the valve orifice or valve leaflets. Remodeling of the annulus is therefore central to most reconstructive procedures for the mitral valve.

As a part of the valve repair, it is desired to either diminish or constrict the involved segment of the annulus so that the leaflets may coapt correctly on closing, or to stabilize the annulus to prevent post operative dilatation from occurring. The current open-heart approach is by implantation of a prosthetic ring, such as a Cosgrove Ring or a Carpentier Ring, in the supra annular position. The purpose of the ring is to restrict and/or support the annulus to correct and/or prevent valvular insufficiency. In tricuspid valve repair, constriction of the annulus usually takes place in the posterior leaflet segment and in a small portion of the adjacent anterior leaflet.

Various prostheses have been described for use in conjunction with mitral or tricuspid valve repair. The ring developed by Carpentier, U.S. Pat. No. 3,656,185, is rigid and flat. An open ring valve prosthesis as described in U.S. Pat. No. 4,164,046 comprises a uniquely shaped open ring valve prosthesis having a special velour exterior for effecting mitral and tricuspid annuloplasty. The fully flexible annuloplasty ring could only be shortened in the posterior segment by the placement of plicating sutures. U.S. Pat. No. 5,674,279 to Wright et al. discloses a suturing ring suitable for use on heart valve prosthetic devices for securing such devices in the heart or other annular tissue. All of the above valve repair or replacement requires an open-heart operation which is costly and exposes a patient to higher risk and longer recovery than a less invasive procedure.

Moderate heat is known to tighten and shrink the collagen tissue as illustrated in U.S. Pat. Nos. 5,456,662 and 5,546,954. It is also clinically verified that thermal energy is capable of denaturing the tissue and modulating the collagenous molecules in such a way that treated tissue becomes more resilient (See "The Next Wave in Minimally Invasive Surgery", *Medical Device & Diagnostic Industry*, pp. 36-44, August 1998). Therefore, it becomes imperative to treat the inner walls of an annular organ structure of a heart valve, a valve leaflet, chordae tendinae, papillary muscles, and the like by shrinking/tightening techniques. The same shrinking/tightening techniques are also applicable to stabilize injected biomaterial to repair the defect annular organ structure, wherein the injectable biomaterial is suitable for penetration and heat initiated shrinking/tightening.

One method of reducing the size of tissues in situ has been used in the treatment of many diseases, or as an adjunct to surgical removal procedures. This method applies appropriate heat to the tissues, and causes them to shrink and tighten. It can be performed in a minimal invasive or percutaneous fashion, which is often less traumatic than surgical procedures and may be the only alternative method, wherein other procedures are unsafe or ineffective. Ablative treatment devices have an advantage because of the use of a therapeutic energy that is rapidly dissipated and reduced to a non-destructive level by conduction and convection, to other natural processes.

Radio frequency (RF) therapeutic protocol has been proven to be highly effective when used by electrophysiologists for the treatment of tachycardia, atrial flutter and atrial fibrillation. It has also been proven effective by neurosurgeons for the treatment of Parkinson's disease, by otolaryngologists for clearing airway obstruction and by neurosurgeons and anesthetists for other RF procedures such as Gasserian ganglionectomy for trigeminal neuralgia and percutaneous cervical cordotomy for intractable pains.

Radiofrequency treatment, which exposes a patient to minimal side effects and risks, is generally performed after first locating the tissue sites for treatment. Radiofrequency energy, when coupled with a temperature control mechanism, can be supplied precisely to the device to tissue contact site to obtain the desired temperature for treating a tissue or for effecting the desired shrinking of the host collagen or injected bioresorbable material adapted to immobilize the biomaterial in place.

U.S. Pat. No. 6,258,087 to Edwards et al. discloses an expandable electrode assembly comprising a support basket formed from an array of spines for forming lesions to treat dysfunction in sphincters. Electrodes carried by the spines are intended to penetrate the tissue region upon expansion of the basket. The assembly disclosed by Edwards et al. does not teach a probe that allows the user to target numerous portions of the heart for treatment while the probe is inserted within the patient.

U.S. Pat. No. 6,355,030 to Aldrich et al. discloses instruments and methods for treating and repairing heart valve structures. Aldrich et al. discloses an apparatus with a handle portion and a heating member in a ring-shaped annular configuration at the distal end of the handle portion. Both the handle portion and the heating member are made from a conformable material which are manipulated by a treating physician to shape the apparatus by hand to fit an individual patient geometries and particular clinical applications. The apparatus shown in Aldrich et al. does not teach that the heating member can be manipulated by a control to target different portions of the heart for treatment while the heating member is within the patient. If the Aldrich apparatus required manipulation by the treating physician, it would have to be first retracted from the patient, then reinserted followed by possible repeated retraction-reinsertion cycles, thus lengthening the surgical procedure and possibly endangering the patient.

Therefore, because of the above mentioned problems and limitations in conventional treatments and surgical devices, there is a need to have less invasive surgical probes and methods for treating structures of the heart including heart valves and for in situ targeted treatment of particular heart structures.

Background of the Invention

One or more embodiments of the invention are directed to surgical probes and methods for targeted treatment of heart structures and more particularly, for a surgical probe and methods that utilizes tissue-shrinkable energy for treating and repairing tissues surrounding anatomic structures within the heart.

In one embodiment, the surgical probe of the present invention is used for repairing an annular organ structure of a patient. The probe has an elongate member adapted to allow insertion of at least a portion of the member into a body vessel. At a distal end of the elongate member, there is an energy-delivering member with an adjustable length that extends from the distal end of the elongate member in an adjustable loop. Energy-delivering elements are operably connected to the energy-delivering member and are powered by energy sources well-known to persons skilled in the art.

A user-operated control is located at the proximal end of the elongate member to adjust the length of the energy delivering member. The energy-delivering elements are placed in communication with selected portions of the organ structure by the user-controlled length adjustments of the energy delivering member and thus the energy-delivering elements supply tissue-shrinkable energy to selected portions of the organ structure and are placed in communication with numerous portions without the need to withdraw the energy-delivering member to re-configure the member to conform to another organ structure. Thus, the same amount of treatment to specific targeted areas can be accomplished in less time.

In one embodiment, the elongate member is comprised of a malleable material to further allow the probe to conform to the anatomy of the heart structure undergoing treatment. In another embodiment, the energy-delivering elements are electrodes and in another embodiment the energy-delivering elements include a radiofrequency source. In an embodiment, the tissue-shrinkable energy is heat energy and in one embodiment the tissue shrinkable energy includes radiofrequency energy.

In one embodiment, the surgical probe has at least one thermocouple in communication with each of the electrodes while in another embodiment, the surgical probe has at least two thermocouples in communication with each of the electrodes.

In one embodiment, the invention includes a method for repairing an annular organ structure of a patient. In this embodiment, the method includes the steps of utilizing a surgical probe by placing at least a portion of the energy-delivering member within a body vessel, placing the energy-delivering elements in communication with selected portions of the organ structure by user-controlled length adjustments of the energy-delivering member through user input to the control and then supplying tissue-shrinkable energy to selected portions of the organ structure that are in communication with said energy-delivering elements.

In one embodiment, the method includes the step where the elongate member is made of a conformable material and configured to further place the energy-delivering elements in communication with the selected portions of the organ structure. The energy-delivering elements can include electrodes and a radiofrequency source.

Other and further objects and advantages will be apparent to persons skilled in the art from the figures and written disclosure including the claims herein.

BRIEF DESCRIPTION OF THE DRAWINGS

Additional objects and features of the present invention will become more apparent and the invention itself will be best understood from the following Detailed Description, when read with reference to the accompanying drawings.

FIG. 1 is one embodiment of a surgical probe of the present invention.

FIG. 2 is a side view of another embodiment of the invention illustrating a malleable elongate member.

FIG. 3 is a side view of one embodiment of the surgical probe of the present invention showing the additional length of the energy-delivering member.

FIG. 4 is a side view of an embodiment of the surgical probe of the present invention showing a withdrawal of the length of the energy-delivering member for positioning of the energy-delivering elements.

FIG. 5 is a side view of one embodiment showing additional retraction of the length of the energy-delivering member for further positioning of the energy-delivering elements.

DETAILED DESCRIPTION OF THE INVENTION

The following descriptions of the preferred embodiment of the invention are exemplary, rather than limiting, and many variations and modifications are within the scope and spirit of the invention. Although numerous specific details are set forth in order to provide a thorough understanding of the present invention, it will be apparent to one of ordinary skill in the art, that embodiments of the invention may be practiced without these specific details. In other instances, well-known features have not been described in detail in order to avoid unnecessarily obscuring the present invention limiting, and many variations and modifications are within the scope of the invention without all of the details or parts described herein.

One or more embodiments of the invention are directed to a surgical probe and methods for targeted treatment of heart structures. FIG. 1 shows an embodiment of the surgical probe 10 of the present invention that has an elongate member 12 with a proximal end 14 and distal end 16. A handle portion 18 is positioned at the proximal end 14 and configured to be grasped by a human operator to manipulate the surgical probe 10. Many different configurations of the handle 18 are possible so as to allow the user control over the surgical probe 10. The handle portion 18 includes a control 20 to permit the user to manipulate the length of the energy delivering member 30 as described more fully below. A power cord 22 is provided that provides power for example, from an external power source.

Positioned at the distal end 16 is the energy-delivering member 30. In an embodiment, the energy-delivering member 30 extends from the distal end 16 in a loop configuration as shown in FIG. 1. In this embodiment, the energy-delivering member 30 exits from the distal end 16 of the elongate member 12 at the first port 30a and loops around and then re-enters the elongate member 12 at the second port 30b.

Located on the energy-delivering member 30 as shown in FIG. 1 are the energy-delivering elements 32. In one embodiment, the energy-delivering elements 32 include electrodes 40 and a radiofrequency source 42. Electrodes 40 well known to persons skilled in the art, are made of platinum and 10% iridium combination, and other metals are also suitable including platinum alone, gold and stainless steel.

In one embodiment, thermocouples 44 are also provided at the electrodes 40 and may include two thermocouples 44 per electrode 40 to sense the temperature at each electrode 40. Typically, the energy-delivering elements include seven electrodes 40 but the present invention includes probes any number of electrodes 40.

In another embodiment, the radiofrequency source 42 delivers energy in the range of 300 kHz to 2.5 MHz and radiofrequency energy sources that are within the range of about 300 kHz to 1 MHz have also shown to be within the scope of the present invention. Readers should also note that in cases where radio frequency is used the mode for delivering such energy can be either mono-polar or bi-polar. Power levels at approximately 50 Watts with a target temperature of 65° C. measured at the interface of the energy-delivering elements 32 and the tissue under treatment have been shown to yield good tissue shrinkage. Temperature ranges from 50° C. to 80° C. as measured at the interface are within the scope of the present invention with treatment times of approximately 60 seconds. Other types of energy delivering elements such as microwave, ultrasound, laser irradiation, or any other energy source able to provide the proper temperature needed to effect tissue shrinkage on heart structures.

In one embodiment, thermocouples 44—are also provided at the electrodes 40 and may include two thermocouples 44—per electrode 40 to sense the temperature at each electrode 40. Typically, the energy-delivering elements include seven electrodes 40 but the present invention includes probes any number of electrodes 40.

FIG. 3 illustrates an embodiment where additional length of the energy-delivering member 30 has been dispensed out via either first port 30a or second port 30b to adjust the position of the energy-delivering elements 32 by use of the control 20. As shown in FIG. 5, this allows for selective placement of the energy-delivering elements 32 on an anatomical structure of the heart or a particular portion of a heart valve for treatment by the energy-delivering elements 32 without the need to withdraw the energy-delivering member 30 from the patient.

FIG. 4 illustrate an embodiment where a portion of the length of the energy-delivering member 30 has been withdrawn in via either first port 30a or second port 30b to place the energy-delivering elements 32 at a different location, for example, to treat a different portion of the heart such as for repairing an annular organ structure of a heart valve, an annular organ structure of a venous valve, a valve leaflet, chordae tendinae, papillary muscles, and the like.

FIG. 5 illustrates a further re-positioning of the energy-delivering elements 32 by withdrawing a further length of the energy-delivering member 30 via either first port 30a or second port 30b. As shown in both FIG. 4 and FIG. 5, the selected positioning of the energy-delivering elements 32 modifies the loop configuration of the energy-delivering member 30 and allows many targeted areas of the heart to be treated without the need to withdraw the energy-delivering member 30 from the patient.

From the foregoing, a surgical probe and methods for treatment of anatomical structures within the heart have been disclosed. While the invention has been described with reference to specific embodiments, the description herein is illustrative of the invention and is not to be construed as limiting the invention to particular embodiments or features. Numerous modifications and applications may occur to persons skilled in the art without departing from the true spirit and scope of the invention as described by the appended claims including the full breadth and scope of equivalents thereof.

What is claimed is:

1. A method for repairing an annular organ structure of a patient using a surgical probe comprising an elongate member having a distal end and a proximal end, an energy-delivering member adjustably extending from the distal end of said elongate member, energy-delivering elements operably connected to said energy-delivering member and a control adjacent to said proximal end, comprising:

placing at least a portion of said energy-delivering member within an annular organ structure of a patient;

placing said energy-delivering elements in communication with selected portions comprising collagen tissue in said annular organ structure by remotely adjust a length of a dispensed portion of said energy-delivering member and a position of energy-delivering elements relative to said dispensed portion by asymmetrically dispensing or withdrawing said energy-delivering member from at least one of a first port and a second port; and supplying tissue-shrinkable energy to the selected portions of the said annular organ structure in communication with said energy-delivering elements to tighten said selected portions.

2. The method of claim 1 wherein said elongate member is configured to place the energy-delivering elements in communication with the selected portions of the organ structure.

3. The method of claim 1 wherein said energy-delivering elements comprise electrodes.

4. The method of claim 3 further comprising the step of providing at least one thermocouple in communication with each of said electrodes.

5. The method of claim 3 further comprising the step of providing at least two thermocouples in communication with each of said electrodes.

6. The method of claim 1 wherein said energy-delivering elements comprise a source configured to deliver radiofrequency energy in a range of between about 300 kHz to about 2.5 MHz.

7. The method of claim 1 wherein said tissue-shrinkable energy comprises heat energy in a range of between about 50° C. to about 80° C.

8. The method of claim 1 wherein said tissue shrinkable energy comprises radio frequency energy in a range of between about 300 kHz to about 1 MHz.

9. The method of claim 1, wherein said energy-delivering member comprises a first end extending from a first port of said elongate member and a second end extending from a second port of said elongate member.

10. The method of claim 9, further comprising remotely adjusting a position of said energy-delivering elements relative to a dispensed portion of said energy-delivering member without withdrawing said energy-delivering member from a body vessel, wherein said position is adjusted by asymmetrically dispensing or withdrawing said energy-delivering member from at least one of said first port and said second port.

11. The method of claim 1, further comprising the step of remotely adjusting a size of said energy-delivering member to change a dispensed length of said energy-delivering member.

\* \* \* \* \*